United States Patent
Ambeck-Madsen et al.

(10) Patent No.: US 12,064,246 B2
(45) Date of Patent: Aug. 20, 2024

(54) METHOD AND SYSTEM FOR DETERMINING A DRIVING INTENTION OF A USER IN A VEHICLE USING EEG SIGNALS

(71) Applicants: TOYOTA MOTOR EUROPE, Brussels (BE); CAMLIN ITALY S.R.L., Parma (IT)

(72) Inventors: Jonas Ambeck-Madsen, Brussels (BE); Luca Ascari, Parma (IT); Luca Kubin, Parma (IT); Marcello Mastroleo, Parma (IT); Maria Del Vecchio, Parma (IT); Roberto Ugolotti, Parma (IT)

(73) Assignees: TOYOTA MOTOR EUROPE, Brussels (BE); CAMLIN ITALY S.R.L., Parma (IT)

( * ) Notice: Subject to any disclaimer, the term of this patent is extended or adjusted under 35 U.S.C. 154(b) by 752 days.

(21) Appl. No.: 16/635,077

(22) PCT Filed: Aug. 3, 2017

(86) PCT No.: PCT/EP2017/069736
§ 371 (c)(1),
(2) Date: Jan. 29, 2020

(87) PCT Pub. No.: WO2019/025000
PCT Pub. Date: Feb. 7, 2019

(65) Prior Publication Data
US 2021/0093241 A1    Apr. 1, 2021

(51) Int. Cl.
A61B 5/18    (2006.01)
A61B 5/00    (2006.01)
A61B 5/372    (2021.01)

(52) U.S. Cl.
CPC ............... *A61B 5/18* (2013.01); *A61B 5/372* (2021.01); *A61B 5/725* (2013.01); *A61B 5/7257* (2013.01); *A61B 5/7267* (2013.01)

(58) Field of Classification Search
None
See application file for complete search history.

(56) References Cited

U.S. PATENT DOCUMENTS 5,598,508 A * 1/1997 Goldman ............. A61B 5/7264
706/20
5,638,826 A * 6/1997 Wolpaw ................. G06F 3/015
345/157

(Continued)

FOREIGN PATENT DOCUMENTS

CN       104127179 A      11/2014
KR    20160095274 A *    8/2016 ............. G06F 3/015

(Continued)

OTHER PUBLICATIONS

Kilicarslan, A., Prasad, S., Grossman, R. G., Contreras-Vidal, J. L. (2013). High accuracy decoding of user intentions using EEG to control a lower-body exoskeleton. 2013 35th Annual International Conference of the IEEE Engineering. doi.org/10.1109/embc.2013.6610821 (Year: 2013).*

(Continued)

*Primary Examiner* — Benjamin S Melhus
*Assistant Examiner* — Samuel C Kim
(74) *Attorney, Agent, or Firm* — Sughrue Mion, PLLC (57) ABSTRACT

A method for determining a driving intention of a user in a vehicle using electroencephalography (EEG) signals, comprising:
acquiring (100) a plurality of EEG signals on a user in the vehicle,
determining (101, ... , 104) a plurality of features of the EEG signals, (Continued)

for each feature of the EEG signals, performing (111, ..., 114') a respective preliminary soft classification process, so as to obtain a plurality of preliminary soft predictions of driving intention each based on a feature of the EEG signals, performing (120) a soft classification process based on the plurality of preliminary soft predictions so as to obtain the driving intention of the user.

10 Claims, 7 Drawing Sheets

(56) References Cited

U.S. PATENT DOCUMENTS

| | | | |
|---|---|---|---|
| 6,070,098 A | 5/2000 | Moore-Ede et al. | |
| 7,127,283 B2 | 10/2006 | Kageyama | |
| 8,447,704 B2* | 5/2013 | Tan | G06F 3/017 |
| | | | 706/62 |
| 2004/0117098 A1 | 6/2004 | Ryu et al. | |
| 2007/0010754 A1 | 1/2007 | Muller et al. | |
| 2007/0265533 A1* | 11/2007 | Tran | A61B 5/7264 |
| | | | 600/528 |
| 2010/0217146 A1 | 8/2010 | Osvath | |
| 2012/0143075 A1* | 6/2012 | Tansey | A61B 5/374 |
| | | | 600/544 |
| 2012/0177233 A1* | 7/2012 | Kidmose | G06F 3/015 |
| | | | 381/314 |
| 2017/0303842 A1* | 10/2017 | Yoshida | B60W 50/14 |
| 2018/0140203 A1* | 5/2018 | Wang | A61B 5/11 |

FOREIGN PATENT DOCUMENTS

| | | |
|---|---|---|
| WO | 2012/102675 A1 | 8/2012 |
| WO | WO-2014092494 A1 * | 6/2014 ......... A61B 5/04845 |

OTHER PUBLICATIONS

Machine Translation of KR 20160095274 A. Retrieved from worldwide.espacenet.com. 2022 (Year: 2022).*

Translation of WO 2014092494 A1. Retrieved from espacenet.com (Year: 2023).*

International Search Report for PCT/EP2017/069736 dated, May 2, 2018 (PCT/ISA/210).

Written Opinion of the International Searching Authority for PCT/EP2017/069736 dated, May 2, 2018 (PCT/ISA/237).

* cited by examiner

METHOD AND SYSTEM FOR DETERMINING A DRIVING INTENTION OF A USER IN A VEHICLE USING EEG SIGNALS

CROSS REFERENCE TO RELATED APPLICATIONS

This application is a National Stage of International Application No. PCT/EP2017/069736 filed Aug. 3, 2017.

FIELD OF THE INVENTION

The present disclosure is related the determination of a driving intention of a user in a vehicle using electroencephalography (EEG) signals.

BACKGROUND OF THE DISCLOSURE

Brain Computer Interfaces (BCI) can be used as interface between a human and an object to be controlled by the brain of a user. Typically, in a Brain Computer Interface, EEG signals are acquired to determine the intention of the user by analyzing the EEG signals.

There has been solutions disclosed in which EEG signals are acquired and inputted to a software component, for example in the field of motor imagery in which the software learns the brain patterns of the user associated with repeated motor thoughts.

Document US 20070010754 discloses a method in which cerebral current signals of a vehicle occupant are acquired. These signals are then used to determine the intention of the occupant in real time. This document does not provide enough details on how to implement its Brain Controlled Interface.

Document U.S. Pat. No. 7,127,283 discloses an apparatus which generates brain wave patterns for comparison with pre-stored brain wave patterns. If there is a match with a pre-stored brain wave pattern, a corresponding operation is performed. This document does not address real-time.

Document US 2004117098 discloses a Brain Computer Interface which acquires a feature using a single electrode at a certain frequency to detect the intention of a driver to act on the brakes so as to start braking before the driver presses the brake pedal. The solution of this document is not robust enough, and only one action can be determined.

In the solutions of the prior art, it is difficult to adapt a Brain Computer Interface to multiple users (or to the same user over time) without the intervention of programmers. This limits the use of Brain Computer Interfaces in real life applications.

This issue is linked to the limited number of features used to ensure real-time performance. Brain Computer Interfaces based on motor intention require the user to mentally perform some prototypical motor tasks, often non-coherent with the task being performed and learnt.

Other important limitations are the reduced number of commands (which must correspond to very easily separable brain patterns) and the high cognitive load imposed to the user to train the system.

It is a primary object of the disclosure to provide methods and system that overcome the deficiencies of the currently available systems and methods.

SUMMARY OF THE DISCLOSURE

The present disclosure overcomes one or more deficiencies of the prior art by proposing a method for determining a driving intention of a user in a vehicle using electroencephalography (EEG) signals, comprising:
acquiring a plurality of EEG signals on a user in the vehicle,
determining a plurality of features of the EEG signals,
for each feature of the EEG signals, performing a respective preliminary soft classification process, so as to obtain a plurality of preliminary soft predictions of driving intention each based on a feature of the EEG signals,
performing a soft classification process based on the plurality of preliminary soft predictions so as to obtain the driving intention of the user.

Thus, contrary to some of the solutions of the prior art, a plurality of features is acquired. These features can be, for example, frequency features.

Determining the driving intention of a user in a vehicle can be used, by way of example, to control the vehicle (for example an automobile), or to control a wheelchair if the vehicle is a wheelchair, or a pod vehicle, or a wearable exoskeleton, or to control the movement of a remote artifact or robotic system which can be driven to move, or of one or more artificial limbs which can also be driven to move Each of these features is associated with a respective preliminary soft classification process. Each preliminary soft classification process is associated with a driving intention. The preliminary soft classification processes can be associated with different or the same driving intention, for example, a first number of preliminary soft classification processes can be associated with the same driving intention and a second number of preliminary soft classification processes can be associated with another driving intention.

A preliminary soft prediction of driving intention may relate to one type of driving intention, for example one action. The final driving intention obtained by the non-preliminary soft classification can be a composite driving intention with a plurality of components each corresponding to one type of driving intention. Alternatively, if all the preliminary soft predictions relate to the same type of driving intention then the non-preliminary driving intention comprises only one component.

In the above method, preliminary soft classification processes do not output binary information relating to a certain driving intention but a value which represents this intention. For example, a preliminary soft classification process can output a value comprised between 0 and 1, with the value 1 corresponding to a high probability of a driving intention being detected and 0 corresponding to a high probability of the absence of this driving intention being detected. For example, a preliminary soft classification process can be associated with the driving intention "turning left" and the associated preliminary soft classification process may output a value approaching 1 if it is detected that the driving intention is turning left or a value approaching 0 if this intention is not detected.

The soft classification process may take as input at least these values outputted by the preliminary soft classification processes so as to output a plurality of values (or components), each value being associated with a possible driving intention provided by the preliminary soft classification processes. If two preliminary soft classification processes are used in relation to "turning left" and one preliminary soft classification process is used in relation to "turning right" then the output of the soft classification process may deliver the driving intention of the user in the form of two values, one for "turning left" comprised between 0 and 1, and one for "turning right" comprised between 0 and 1.

It should be noted that the soft classification process outputs a driving intention of the user in the form of a number of values each corresponding to a possible driving intention (the driving intention are the possible driving intentions used by the preliminary soft classification processes).

The use of (preliminary) soft classification processes allows using processes which can work in real-time so as to obtain the driving intention of a user in a timely manner. Thus, the above method can be a real-time method.

Also, (preliminary) soft classification processes can be trainable (using the principles known to the skilled person as machine learning) and thus can be adapted to each user in a training phase. Such a training may not require the intervention of a programmer and is easy to implement.

By real-time, it is meant that the driving intention of the user can be obtained in a duration which may be less than the duration between the cognitive decision and the actual corresponding action. For example, this duration can be of the order of 200 to 400 milliseconds, and this range of durations corresponds to the durations between anticipatory brain correlates in response to a stimulus (response to other's behaviors, traffic or road conditions, . . . ) and the actual movement.

According to an embodiment, each determination of a feature of the EEG signals comprises pre-processing the EEG signals in which a band-pass filter is applied to the signals, wherein the band-pass filter passes frequencies within the $\alpha$ band, or the $\beta$ band, or the $\alpha$ band and the $\beta$ band.

The $\alpha$ band and the $\beta$ band are frequency bands well known to the skilled person which respectively correspond to 8 to 12 Hertz and to 18 to 22 Hertz. These bands are usually associated with motor-rhythms in the central-parietal part of the brain. Thus, these bands contain signals from which features can be obtained to determine the driving intention of a user.

According to an embodiment, the pre-processing comprises applying a common average reference treatment.

A common average reference treatment may consist in referencing each EEG signal (sometimes referred to as a channel) with respect to the average (for example a moving or rolling average) of all or a subset of the signals. By referencing, it is meant that the common average is subtracted. This treatment has been seen to improve the performance of (preliminary) soft classification processes for at least some users. This treatment notably improves the signal to noise ratio of the signals.

According to an embodiment, the features are chosen from the group comprising: variances of the EEG signals, entropy values of the EEG signals, the short-term Fourier transform of the EEG signals, and covariances of the EEG signals.

According to an embodiment, the features are chosen from the group comprising event related spectral perturbations, instantaneous phase shift, to measure event-locked changes in spectral power and phase, extracted from EEG signals.

According to an embodiment, the features are chosen from the group comprising event related spectral perturbations, instantaneous phase shift, to measure event-locked changes in spectral power and phase, extracted from independent EEG components.

The skilled person will know how to obtain these features, and it is possible to determine corresponding driving intentions through tests and calibrations.

The inventors of the present disclosure have observed that these features can provide good information on the driving intention of the user.

According to an embodiment, the preliminary soft predictions of driving intentions are preliminary soft predictions of at least one driving intention chosen from the group comprising: an intention to move or rest, an intention to turn left, an intention to turn right, an intention to accelerate, and an intention to brake.

According to an embodiment:
if the feature corresponds to variances, a preliminary soft classification is performed so as to obtain a preliminary soft prediction of an intention to move or rest based on the variances,
if the feature corresponds to differential entropy values, a preliminary soft classification is performed so as to obtain a preliminary soft prediction of an intention to move or rest based on the differential entropy values,
if the feature corresponds to the short-term Fourier transform,
a preliminary soft classification is performed so as to obtain a preliminary soft prediction of an intention to turn left based on the short-term Fourier transform,
a preliminary soft classification is performed so as to obtain a preliminary soft prediction of an intention to turn right based on the short-term Fourier transform,
a preliminary soft classification is performed so as to obtain a preliminary soft prediction of an intention to accelerate based on the short-term Fourier transform, and
a preliminary soft classification is performed so as to obtain a preliminary soft prediction of an intention to brake based on the short-term Fourier transform,
if the feature corresponds to covariances,
a preliminary soft classification is performed so as to obtain a preliminary soft prediction of an intention to turn left based on the covariances,
a preliminary soft classification is performed so as to obtain a preliminary soft prediction of an intention to turn right based on covariances,
a preliminary soft classification is performed so as to obtain a preliminary soft prediction of an intention to accelerate based on the covariances, and
a preliminary soft classification is performed so as to obtain a preliminary soft prediction of an intention to brake based on the covariances.

According to an embodiment, performing a soft classification process to the plurality of preliminary soft predictions so as to obtain the driving intention of the user comprises using a multilayer perceptron.

The use of a multilayer perceptron allows obtaining good results. It should be noted that performing a soft classification process to the plurality of preliminary soft predictions so as to obtain the driving intention of the user can comprise using other types of classifiers which exploit non linear relations.

According to an embodiment, the method comprises using a naive Bayes Gaussian classification layer on the preliminary soft predictions to obtain additional preliminary soft predictions each corresponding to a possible driving intention (do nothing, accelerate, brake, turn left, turn right), the additional preliminary soft predictions and the preliminary soft predictions being used as input to the soft classification process.

Using a naive Bayes Gaussian classification layer facilitates the subsequent soft classification by automatically finding and classifying the points outputted by the preliminary soft classification processes. These points are classified around normally distributed clouds, which facilitates the subsequent soft classification.

Using both the additional preliminary soft predictions and the preliminary soft predictions as input to the soft classification process allows preventing outliers discarded by the naive Bayes Gaussian classification layer to be lost for the soft classification process.

According to an embodiment, the method comprises applying at least one delay to the preliminary soft predictions and, if a Bayes Gaussian layer is used, the additional preliminary soft predictions so as to obtain at least one additional input to the soft classification process.

For example, a delay of 0.4 second can be applied to obtain a first additional input and an additional delay of 0.4 second can be applied to this additional input to obtain a second additional input. The signals entering the soft classification process are, in this example:

first input: the preliminary soft predictions and, if a Bayes Gaussian layer is used, the additional preliminary soft predictions,
second input: the first input with a delay of 0.4 second, and
third input: the second input with a delay of 0.4 second.

These steps, often referred to as "embedding", aim at inputting temporal context to the soft classification process. For example, if a multi-layer perceptron is used, it will take time into account even if it was initially designed as a non-time-aware soft classification process.

According to an embodiment, the preliminary soft classification process and the soft classification process have been trained in a prior training step.

Thus, these processes are trainable and belong to the field of machine learning.

The disclosure also provides a system for determining a driving intention of a user in a vehicle using electroencephalography (EEG) signals, comprising:
an acquisition module of a plurality of EEG signals on a user in the vehicle,
a processor,
a memory comprising instructions executable by the processor to:
acquire, using the acquisition module, a plurality of EEG signals on a user in the vehicle,
determine a plurality of features of the EEG signals,
for each feature of the EEG signals, perform a respective preliminary soft classification process, so as to obtain a plurality of preliminary soft predictions of driving intention each based on a feature of the EEG signals,
perform a soft classification process based on the plurality of preliminary soft predictions so as do obtain the driving intention of the user.

This system can be configured to carry out all the embodiments of the method for determining a driving intention of a user in a vehicle as described above.

In one particular embodiment, the steps of the method for determining a driving intention of a user in a vehicle are determined by computer program instructions.

Consequently, the invention is also directed to a computer program for executing the steps of a method as described above when this program is executed by a computer.

This program can use any programming language and take the form of source code, object code or a code intermediate between source code and object code, such as a partially compiled form, or any other desirable form.

The invention is also directed to a computer-readable information medium containing instructions of a computer program as described above.

The information medium can be any entity or device capable of storing the program. For example, the medium can include storage means such as a ROM, for example a CD ROM or a microelectronic circuit ROM, or magnetic storage means, for example a diskette (floppy disk) or a hard disk.

Alternatively, the information medium can be an integrated circuit in which the program is incorporated, the circuit being adapted to execute the method in question or to be used in its execution.

BRIEF DESCRIPTION OF THE DRAWINGS

How the present invention may be put into effect will now be described by way of example with reference to the appended drawings, in which.

DESCRIPTION OF THE EMBODIMENTS

An exemplary method and system for determining a driving intention will be described hereinafter.

In the present description, the driving intention of the user refers to a soft prediction, for example one or more values comprised between 0 and 1 each associated with the probability of an action being carried out by the user.

Also, in the present description, an improvement of the results or better results for the method refer to an improvement in the prediction of the intention of the user observed for example in a training or calibration step (in which it is possible to compare the prediction with the actual action of the user).

Figure 1:
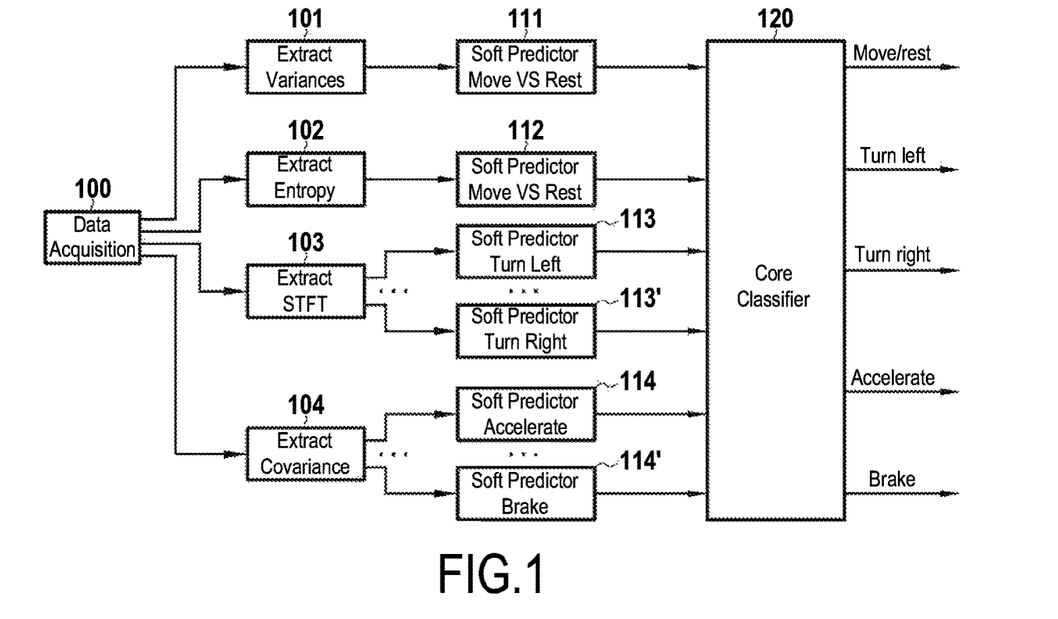
FIG. 1 is a block diagram of an exemplary method for determining a driving intention of a user in a vehicle using EEG signals.

A method for determining a driving intention of a user in a vehicle using electroencephalography (EEG) signals is represented on FIG. 1.

EEG signals can be acquired (step 100 on FIG. 1) in a traditional manner by placing a plurality of electrodes on the head of a user to obtain signals illustrating the electrical activity of the brain of the user. These EEG signals can be obtained while the user is in a vehicle, for example an automobile, and more precisely while the user is in a position to drive the vehicle (for example an automobile).

The acquired EEG signals of FIG. 1 can be referred to as EEG channels by the person skilled in the art.

The acquisition step 100 is performed in real time, and, for example, a total of 19 signals can be obtained.

The EEG signals obtained in step 100 are used in the illustrated example in four determination steps to obtain features of the EEG signals.

A first determination step 101 corresponds to the determination of the variances of the EEG signals (for example one variance value per channel). These variances correspond to a first feature of the EEG signals. This step is followed by a preliminary soft classification process 111, which is illustrated in FIG. 1 as an operation of a soft predictor, to obtain a soft prediction of whether the user's driving intention is directed at moving (performing an action such as turning, accelerating, braking) or resting (not performing a specific action using the vehicle, for example maintaining direction and speed). The soft classification process 111 uses the variances as input.

A second determination step 102 corresponds to the determination of the differential entropy values of the EEG signals. These differential entropy values correspond to a second feature of the EEG signals. This step is followed by a preliminary soft classification process 112, which is illustrated in FIG. 1 as an operation of a soft predictor, to obtain a soft prediction of whether the user's driving intention is directed at moving (performing an action such as turning, accelerating, braking) or resting (not performing a specific action using the vehicle, for example maintaining direction and speed). The soft classification process 112 uses the differential entropy values as input.

It has been observed that the variances and the differential entropy values can be used to discriminate the intention of the user between moving and resting.

A third determination step 103 corresponds to the determination of the short-term Fourier transform (STFT) of the EEG signals. The STFT correspond to a third feature. This step is followed by four preliminary soft classification processes 113, . . . , 113' (only two have been represented on the figure), each of which is illustrated in FIG. 1 as an operation of a soft predictor, to obtain four soft predictions of whether the user's driving intention is directed at:
Turning right,
Turning left,
Accelerating, and
Braking.

The preliminary soft classification processes 113, . . . , 113' use STFT as input.

It has been observed that the STFT can be used to predict these four driving intentions.

A fourth determination step 104 corresponds to the determination of the covariances. The covariances correspond to a fourth feature. This step is followed by four preliminary soft classification processes 114, . . . , 114' (only two have been represented on the figure), each of which is illustrated in FIG. 1 as an operation of a soft predictor, to obtain four soft predictions of whether the user's driving intention is directed at:
Turning right,
Turning left,
Accelerating, and
Braking.

The preliminary soft classification processes 114, . . . , 114' use feature corresponding to covariances as input.

The outputs (the soft predictions) of the preliminary soft classification processes 111 to 114' are inputted to a soft classification process 120, which is illustrated in FIG. 1 as an operation of a core classifier, which will deliver the driving intention of the user in the form of five soft predictions of the driving intention of the user:
moving or resting
Turning right,
Turning left,
Accelerating, and
Braking.

These five soft predictions are obtained because all the preliminary soft classification processes deliver predictions on at least these driving intentions.

The steps of the methods described in reference to FIG. 1 can be determined by computer instructions. These instructions can be executed on a processor of a system, as represented on FIG. 2.

Figure 2:
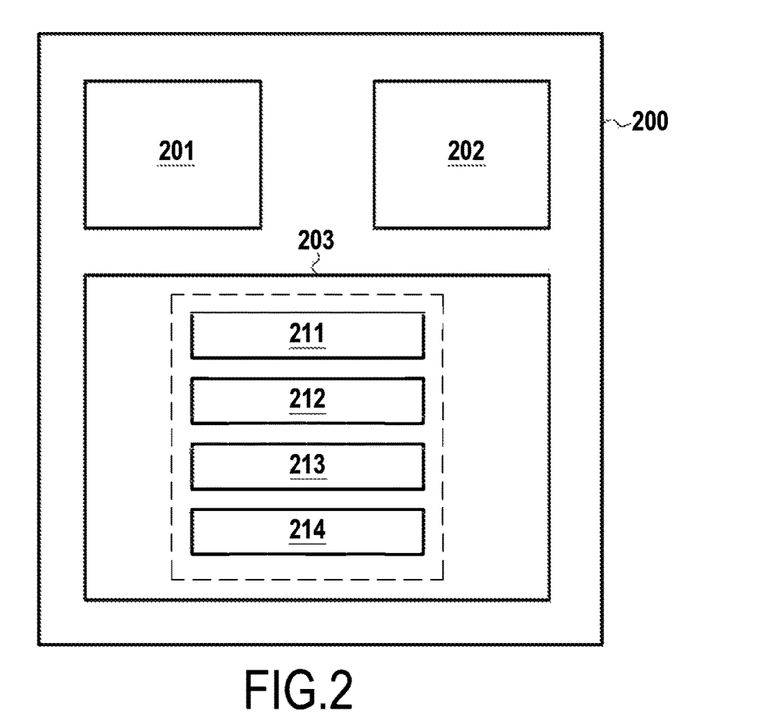
FIG. 2 is a schematic diagram of a system for determining a driving intention of a user in a vehicle using EEG signals

On this figure, a system 200 has been represented. This system comprises a processor 201, an acquisition module 202 of a plurality of a plurality of EEG signals on a user in the vehicle, and a memory 203.

This acquisition module 202 can comprise a connection, wired or wireless, interface with the electrodes which may be connected to the user. It may also comprise amplification modules so as to obtain the EEG signals.

The memory 203 can be a non-volatile memory and it comprises a set of instructions (or computer program) INST which can be executed by the processor 201 to perform the method described in reference to FIG. 1. The set of instructions INST comprises:
  a first instruction 211 to acquire, using the acquisition module, a plurality of EEG signals on a user in the vehicle,
  a second instruction 212 to determine a plurality of features of the EEG signals,
  a third instruction 213 to, for each feature of the EEG signals, perform a respective preliminary soft classification process, so as to obtain a plurality of preliminary soft predictions of driving intention each based on a feature of the EEG signals,
  a fourth instruction 214 to perform a soft classification process based on the plurality of preliminary soft predictions so as to obtain the driving intention of the user.

Figure 3:
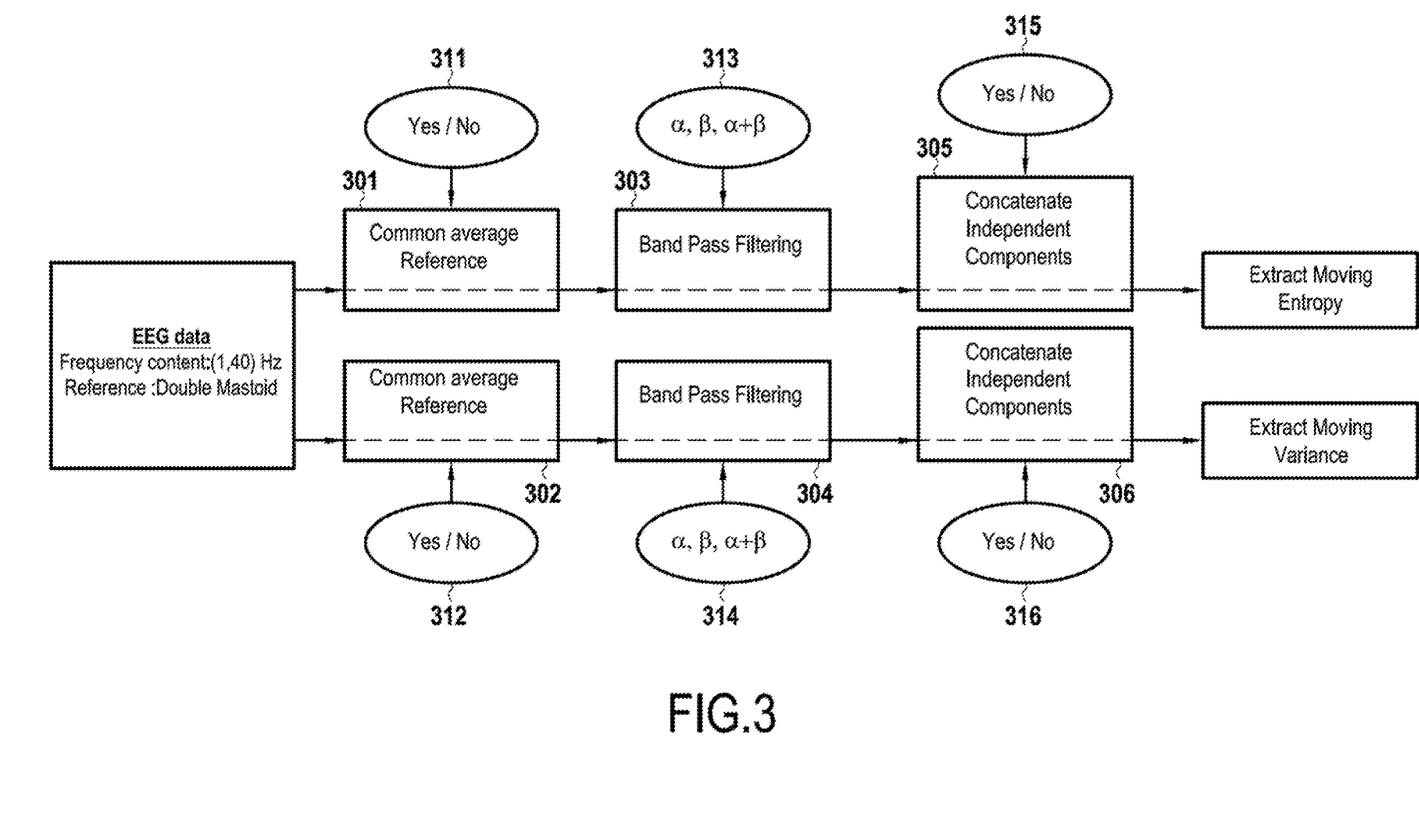
FIG. 3 is a block diagram of the pre-processing for the variances and the differential entropy.

FIG. 3 is a block diagram of the pre-processing performed before determining the variances and the differential entropy values. The pre-processing for the variances and the pre-processing for the differential entropy values are similar. However, because these steps can use different parameters as additional input, it should be noted that the two pre-processing steps are preferably carried out separately (as represented on FIG. 3).

The pre-processing of the differential entropy is performed in real-time. In a first step 301 a common average reference treatment is applied to the EEG signals. This treatment can comprise referencing each EEG signal with respect to the average of all or a subset of the signals, this subset being the result of an off-line and/or on-line assessment of the quality of the signal being recorded. The step 301 is performed optionally, depending on the value of the parameter 311 which indicates whether or not this step should be performed. The value of the parameter 311 can be set during a training or an automatic calibration step so as to determine whether or not the common average reference treatment improves the results for the user on which the method is going to be applied after the training/calibration.

A second step 303 is then carried in which a band-pass filter is applied to the signals. The band-pass filter passes frequencies within the α band, or the β β band, or the α band and the β band. The selection of the band of frequencies can be selected using parameter 313. The value of the parameter 313 (α band, β band, or α and β bands) can be set during a training or an automatic calibration step so as to determine which frequency band improves the results for the user on which the method is going to be applied after the training/calibration.

A third step 305 is performed in which the independent components of the EEG signals are obtained and concatenated to the EEG signals. It should be noted that an independent component analysis is not performed in real time, however, it can be performed during an automatic calibration step on EEG signals which have been recorded (for example on the user). This calibration step can deliver the linear combinations to perform on the EEG signals in real time to obtain the independent components, and these linear combinations can be performed again in real time.

It should be noted that if there are 19 EEG signals then after the execution of step 305 there are 38 EEG signals (19 have been added corresponding to the independent components).

Step 305 is performed optionally, depending on the value of the parameter 315 which indicates whether or not this step should be performed. The value of the parameter 315 can be set during a training or an automatic calibration step so as to determine whether or not adding the independent components improves the results for the user on which the method is going to be applied after the training/calibration.

Concerning the variance, step 302 can be performed to apply a common average reference treatment to the EEG signals (this step is performed optionally, taking parameter 312 into account. The value of the parameter 311 can be set during a training or an automatic calibration step so as to determine whether or not the common average reference treatment improves the results for the user on which the method is going to be applied after the training/calibration.

Step 304 is then carried out in which a band-pass filter is applied to the signals. The band-pass filter passes frequencies within the α band, or the β band, or the α band and the β band. The selection of the band of frequencies can be selected using parameter 314. The value of the parameter 314 (α band, β band, or α and β bands) can be set during a training or an automatic calibration step so as to determine which frequency band improves the results for the user on which the method is going to be applied after the training/calibration.

Step 306 is then carried out in which the independent components are obtained and concatenated to the EEG signals. The step 306 is performed optionally, depending on the value of the parameter 316 which indicates whether or not this step should be performed. The value of the parameter 316 can be set during a training or an automatic calibration step so as to determine whether or not adding the independent components improves the results for the user on which the method is going to be applied after the training/calibration.

Figure 4:
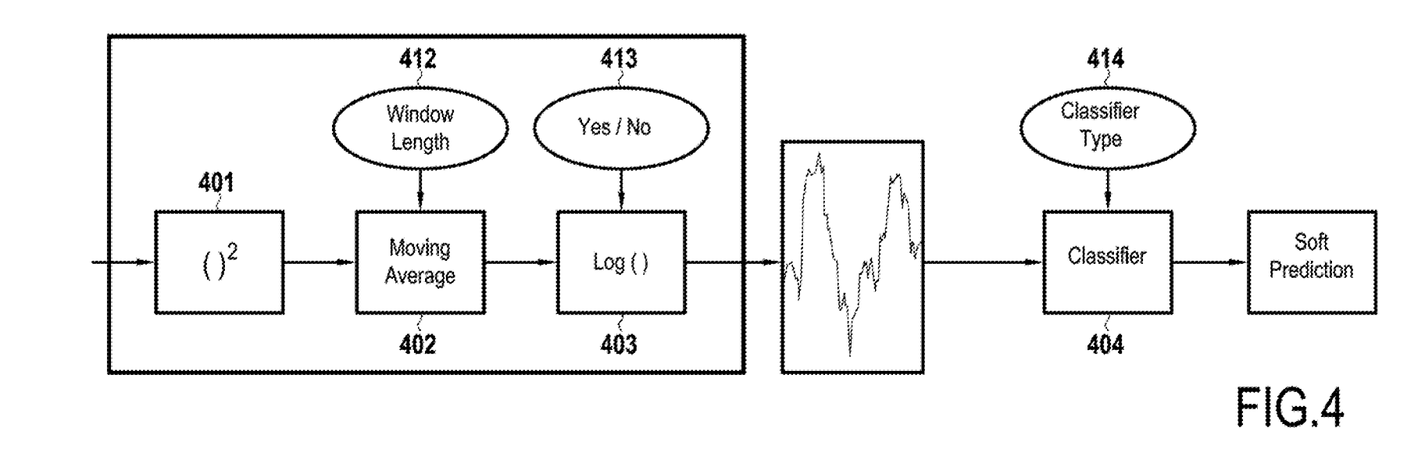
FIG. 4 is a block diagram of the obtaining of a feature corresponding to the variances and the corresponding preliminary soft classification.

FIG. 4 is a block diagram of the obtaining of variances and the corresponding preliminary soft classification.

The steps of this figure are performed after the post-processing described in reference to FIG. 3 has been performed, namely after steps 302, 304 and 306 have been performed.

Thus, at this stage, there are 38 signals if the independent components were added.

In a first step 401, all the signals (i.e. the 38 signals) are squared, which allows obtaining the instantaneous EEG power. Then a moving average is calculated (step 402). This process can consist in calculating the average of the signal over the duration of the window. The window can be rectangular.

The determination of the moving average is done by calculating the average value of the signals over a predetermined duration (for example 0.25 second, 0.5 second, 0.75 second, 1.0 second, 1.5 second).

These durations can be set during a an automatic calibration step, or can depend on the application and the quantity of memory required to perform the calculation. The duration is set in parameter 412.

The average power of the EEG signals is obtained, and these values corresponds to the variance (or moving variance) of each EEG signal (including the variance of the independent components).

Then, a subsequent step 403 is carried out in which the logarithm with base 10 function can be applied to the signals. It has been observed that this function can highlight the differences in the dynamic of the average power.

Step 403 can be performed optionally, depending on the value of the parameter 413 which indicates whether or not this step should be performed. The value of the parameter 413 can be set during a training or an automatic calibration step so as to determine whether or not calculating the logarithm with base 10 improves the results for the user on which the method is going to be applied after the training/calibration.

The variances obtained (or the corresponding logarithmic values) are used as input to a preliminary soft classification process 404 so as to obtain a preliminary soft prediction of whether the user intends to move or rest.

Various types of preliminary soft classification processes can be used for step 404. For example, it is possible to use linear discriminant analysis, quadratic discriminant analysis, support vector machine, logistic regression, or a multi-layer perceptron. These preliminary soft classification processes have to be trained during a training step (preferentially on the user on which the method is going to be applied).

It should be noted that the type of preliminary soft classification process to be used in specified in parameter 414.

Step 414 delivers a soft output, for example a value comprised between 0 (resting) and 1 (moving).

Figure 5:
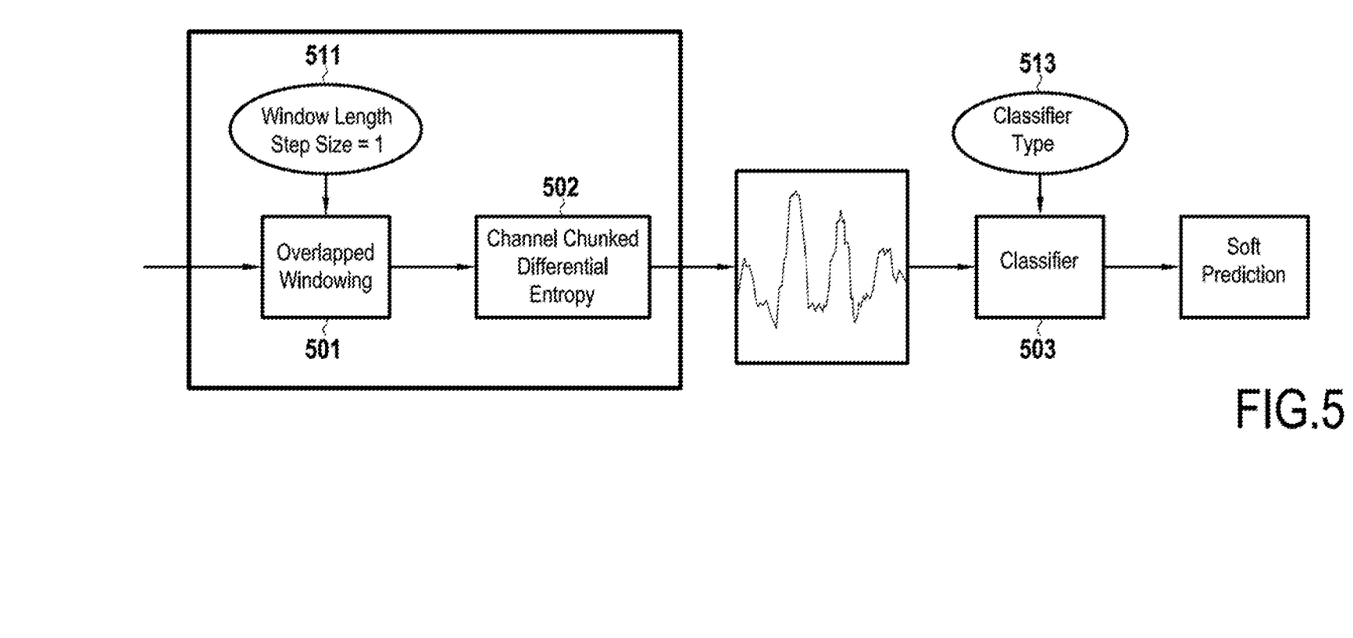
FIG. 5 is a block diagram of the obtaining of a feature corresponding to the differential entropy and the corresponding preliminary soft classification.

FIG. 5 is a block diagram of the obtaining of the differential entropy (or moving differential entropy) of the EEG signals and the corresponding preliminary soft classification.

The steps of this figure are performed after the post-processing described in reference to FIG. 3 has been performed, namely after steps 301, 303 and 305 have been performed.

Thus, at this stage, there are 38 signals if the independent components were added.

In a first step 501, a plurality of windows of EEG signals is determined. More precisely, on each EEG signal, consecutive windows of signal are obtained, and consecutive windows overlap each other.

The length of the windows and the length of the overlapping can be set in parameter 511. For example, the window length can be 0.25 second, 0.5 second, 0.75 second, 1.0 second, 1.5 second. The overlapping can be of the duration of one sample.

A calculation is then performed in step 502. The following formula is used:

$$h(X) = -\int_X f(x) \log(f(x)) dx$$

wherein:
h(X) is the differential entropy,
X is an EEG signal, and
f(x) is its probability density function.

X is band pass filtered (block 304), with a very high probability that its distribution is gaussian (as proved by the result of the adopted Kolmogorov-Smirnov test method, known to the skilled person). Within the Gaussian hypothesis, the formula becomes, for the i-th frequency band:

$$h_i(X) = \tfrac{1}{2}\log(2\pi e \sigma^2)$$

where $\sigma^2$ is the variance.

The differential entropy obtained using the calculation of step 502 is then inputted to a preliminary soft classification process 503 which is able to deliver preliminary soft prediction on whether the user's intention is to move or to rest.

Various types of preliminary soft classification processes can be used for step 503. For example, it is possible to use linear discriminant analysis, quadratic discriminant analysis, support vector machine, logistic regression, or a multi-layer perceptron. These preliminary soft classification processes have to be trained during a training step (preferentially on the user on which the method is going to be applied).

It should be noted that the type of preliminary soft classification process to be used in specified in parameter 513.

Figure 6:
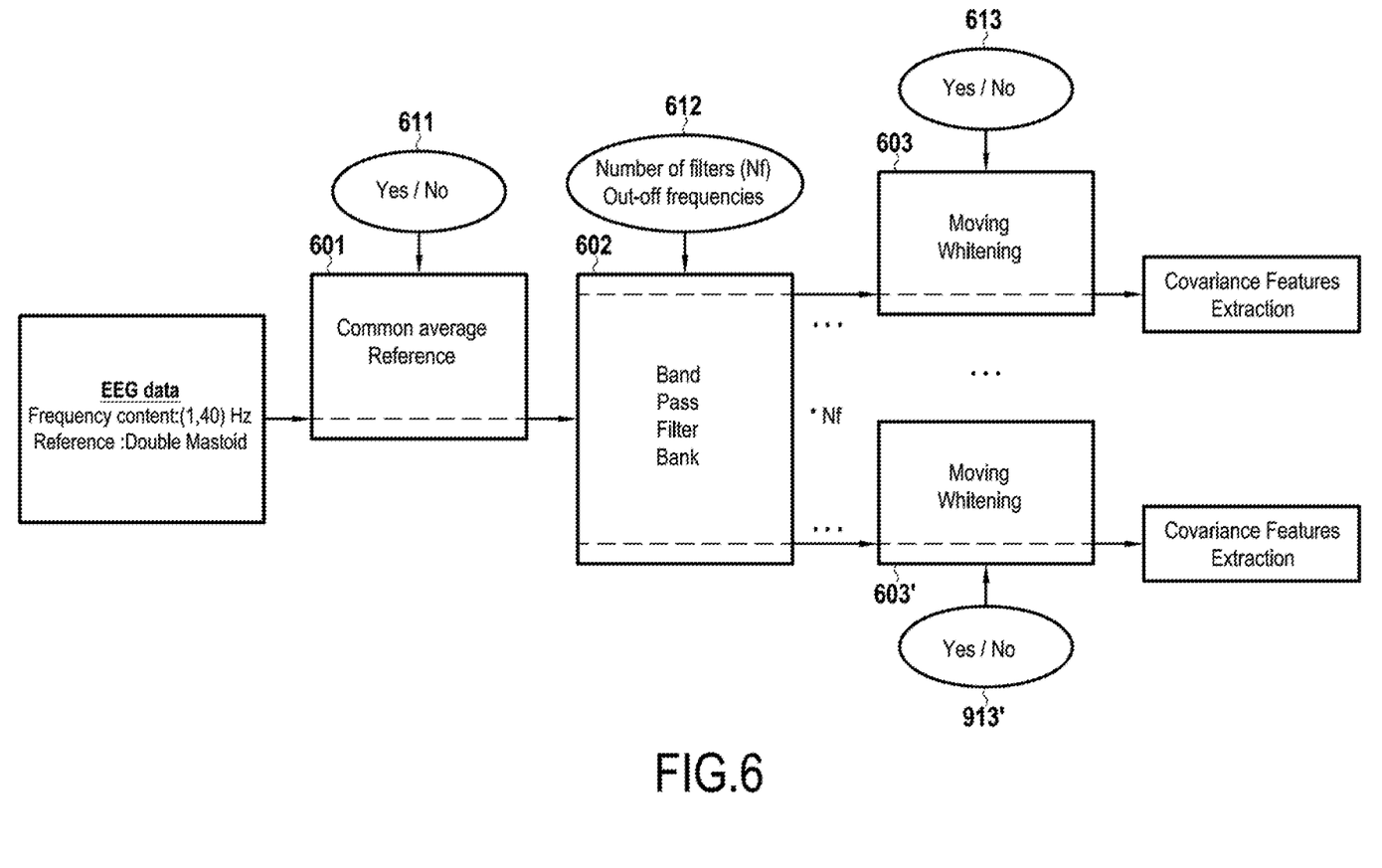
FIG. 6 is a block diagram of the pre-processing for the covariances.

FIG. 6 is a block diagram of the pre-processing performed before the determination of the covariances.

The pre-processing for the covariances is performed in real-time. In a first step 601 a common average reference treatment is applied to the EEG signals. This treatment can comprise referencing each EEG signal with respect to the average of all the signals. The step 601 is performed optionally, depending on the value of the parameter 611 which indicates whether or not this step should be performed. The value of the parameter 611 can be set during a training or an automatic calibration step so as to determine whether or not the common average reference treatment improves the results for the user on which the method is going to be applied after the training/calibration.

Then, step 602 is carried out in which the EEG signals are passed through a plurality of filters (for example N filters) forming a filter bank.

By way of example, four band-pass filters can be used with the following frequencies: [8, 12], [18, 22], [8, 22], and [1, 5] Hz.

If there are 19 EEG signals, then the output of step 602 will comprise 19 times N signals.

The number of filters and their cut-off frequencies form parameter 612. Parameter 612 can be set during a training or an automatic calibration step so as to determine which number of filters and which cut-off frequencies improves the results for the user on which the method is going to be applied after the training/calibration.

Then, each signal can be processed through a moving whitening (steps 613, ..., 613', only two are represented but there is one per signal). A moving whitening process can be applied for obtaining a signal with a moving mean of zero and a unitary standard deviation. This improves the signal stationarity.

The moving whitening processes are optional, depending on the value of the parameter 613, ..., 613' which indicate whether or not this step should be performed. The value of the parameters 613, ..., 613' can be set during a training or an automatic calibration step so as to determine whether or not the moving whitening processes improve the results for the user on which the method is going to be applied after the training/calibration.

Figure 7:
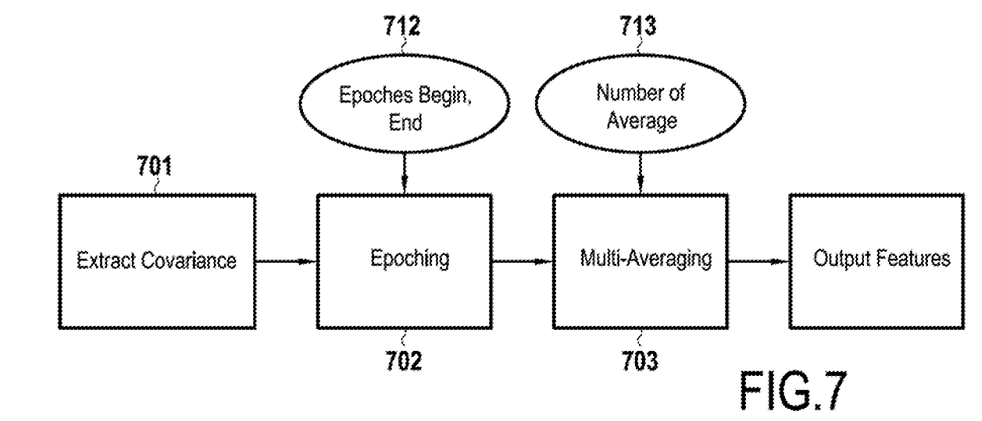
FIG. 7 is a block diagram of the obtaining of a feature corresponding to the covariances.

The determination of a feature corresponding to the covariances is shown on FIG. 7. A first step is carried out in which for each frequency band defined by a filter of step 602 described in reference to FIG. 6, the cross product of all the signals being associated with a same frequency band is determined.

Thus, if there are initially 19 EEG signals and N filters in step 602, there are N*((19+1)*19/2) signals obtained after step 701 so as to obtain a covariance matrix Then, a step of epoching 702, known in itself by the person skilled in the art, is performed on the signals obtained after step 701. This step can be performed by obtaining windows of signal having a predetermined length on each signal. Subsequent windows are obtained as overlapping windows because the step is a real-time step.

The length of the windows (parameter 712) is determined during a training step in which windows of signal are obtained around the time of the actual action (turning left, turning right, accelerating, braking . . . ).

A number of epochs or windows is obtained.

Then, a multi-averaging step 703 is carried out on each epoch or window.

In this step 703, each window or epoch is divided in a predetermined number of non-overlapping segments (for example 3 segments) having the same length. The average of each signal in each segment is determined and these averages are inputted to the preliminary soft classification process.

The number of segments is a parameter 713 to the step 703, and it can be determined during a training step so as to determine whether which number of segment improves the results for the user on which the method is going to be applied after the training/calibration.

The averaged epochs or windows corresponding to the covariances are then inputted to four preliminary soft classification processes (not shown on the figures):

A first soft classification process which delivers a preliminary soft prediction of whether or not the user intends to turn right, A second soft classification process which delivers a preliminary soft prediction of whether or not the user intends to turn left, A third soft classification process which delivers a preliminary soft prediction of whether or not the user intends to accelerate, A fourth soft classification process which delivers a preliminary soft prediction of whether or not the user intends to brake.

Various types of preliminary soft classification processes can be used. For example, it is possible to use linear discriminant analysis, quadratic discriminant analysis, support vector machine, logistic regression, or a multi-layer perceptron. These preliminary soft classification processes have to be trained during a training step (preferentially on the user on which the method is going to be applied).

Figure 8:
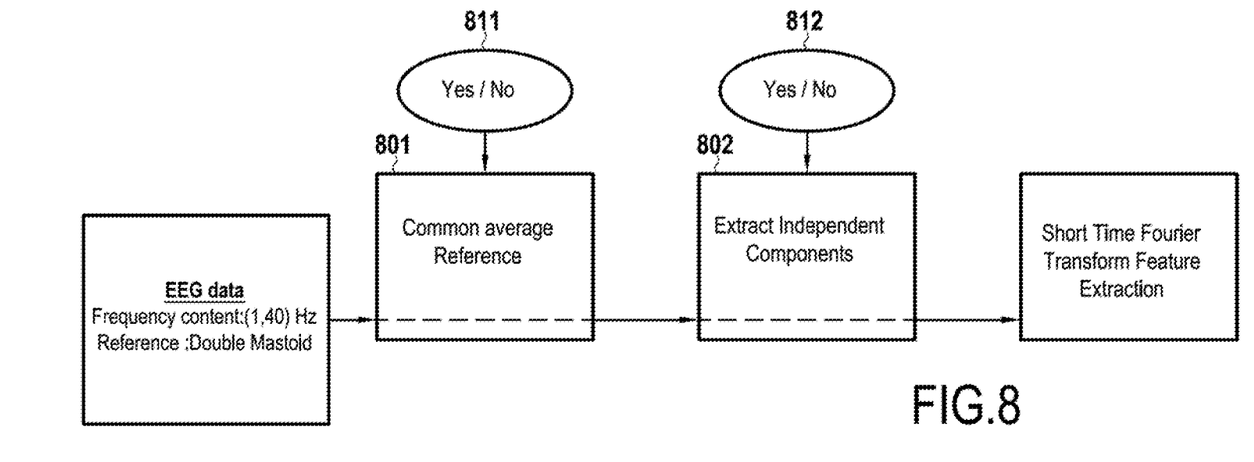
FIG. 8 is a block diagram of the pre-processing for the short-term Fourier transform.

FIG. 8 is a block diagram of the pre-processing performed before the determination of the short-term Fourier transform (STFT) of the EEG signals.

The pre-processing for the STFT is performed in real-time. In a first step 801 a common average reference treatment is applied to the EEG signals. This treatment can comprise referencing each EEG signal with respect to the average of all the signals. The step 801 is performed optionally, depending on the value of the parameter 811 which indicates whether or not this step should be performed. The value of the parameter 811 can be set during a training or an automatic calibration step so as to determine whether or not the common average reference treatment improves the results for the user on which the method is going to be applied after the training/calibration.

A second step 802 is performed in which the independent components of the EEG signals are obtained. It should be noted that an independent component analysis is not performed in real time, however, it can be performed during a an automatic calibration step on EEG signals which have been recorded (for example on the user). This calibration step can deliver the linear combinations to perform on the EEG signals to obtain the independent components, and these linear combinations can be performed again in real time.

It should be noted that if there are 19 EEG signals then after the execution of step 802 there are 19 independent components obtained from the EEG signals. It is not necessary to concatenate the EEG signals to the independent components and it should be noted that this would require a high computational effort in subsequent steps.

The step 802 is performed optionally, depending on the value of the parameter 812 which indicates whether or not this step should be performed. The value of the parameter 812 can be set during a training or an automatic calibration step so as to determine whether or not adding the independent components improves the results for the user on which the method is going to be applied after the training/calibration.

Figure 9:
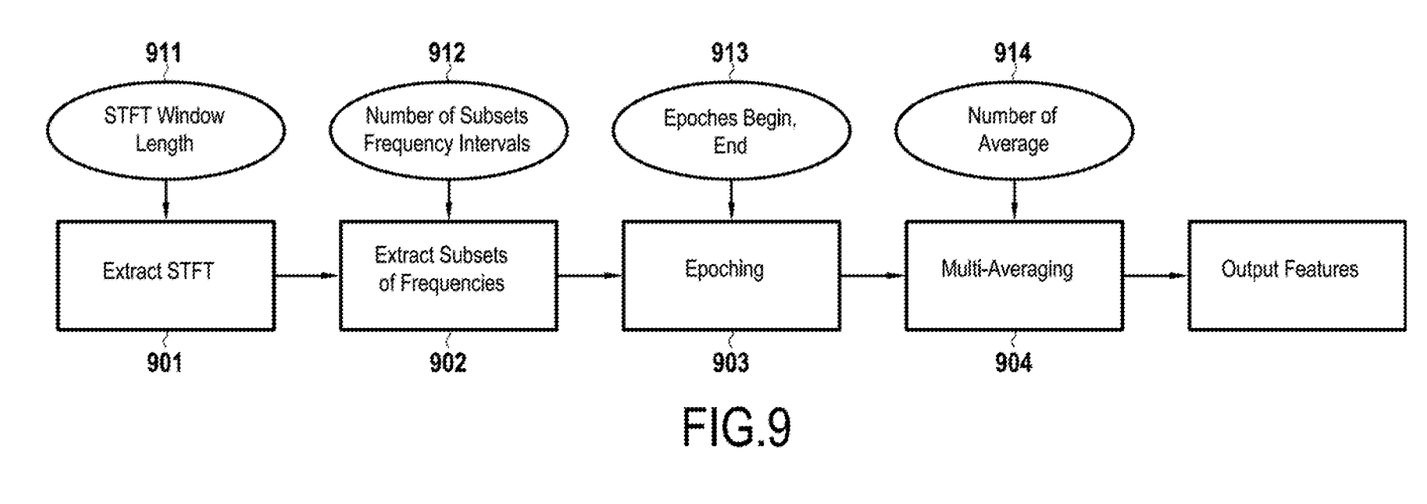
FIG. 9 is a block diagram of the obtaining of a feature corresponding to the short-term Fourier transform.

The determination of the STFT is shown on FIG. 9.

In step 901, the EEG signals (or the independent components if step 802 of FIG. 8 is performed) undergo the extraction of the STFT. This step comprises the obtaining of a window of the inputted signals having a predetermined length (for example set during a training step, for example 0.25 second, 0.5 second, 1.0 second, or 2.0 second) on which the STFT is determined. The duration of the window forms parameter 911 and the value of parameter 911 can be set during a training or an automatic calibration step so as to determine which duration improves the results for the user on which the method is going to be applied after the training/calibration.

Then, once in the frequency domain, in step 902, one or more subsets of signal of the frequencies is extracted to obtain time series in the time domain. For example, the subsets can be the following: [8, 12], [18, 22], [8, 22] and [1, 5] Hz. The number of subsets and the corresponding frequencies can be chosen so as to discriminate better the different driving intentions. Thus, parameter 912 (formed by the number of subsets and the corresponding frequencies) can be determined during the training.

An epoching step 903 is then carried out on the time series to obtain epochs or windows.

Step 904 is then carried out

Then, a multi-averaging step 904 is carried out on each epoch or window.

In this step 904, each window or epoch is divided in a predetermined number of non-overlapping segments (for example 3 segments) having the same length. The average of each signal in each segment is determined and these averages are inputted to the preliminary soft classification process.

The averaged epochs or windows corresponding to the STFT are then inputted to four preliminary soft classification processes (not shown on the figures):
   A first soft classification process which delivers a preliminary soft prediction of whether or not the user intends to turn right,
   A second soft classification process which delivers a preliminary soft prediction of whether or not the user intends to turn left,
   A third soft classification process which delivers a preliminary soft prediction of whether or not the user intends to accelerate,
   A fourth soft classification process which delivers a preliminary soft prediction of whether or not the user intends to brake.

Various types of preliminary soft classification processes can be used. For example, it is possible to use linear discriminant analysis, quadratic discriminant analysis, support vector machine, logistic regression, or a multi-layer perceptron. These preliminary soft classification processes have to be trained during a training step (preferentially on the user on which the method is going to be applied).

Figure 10:
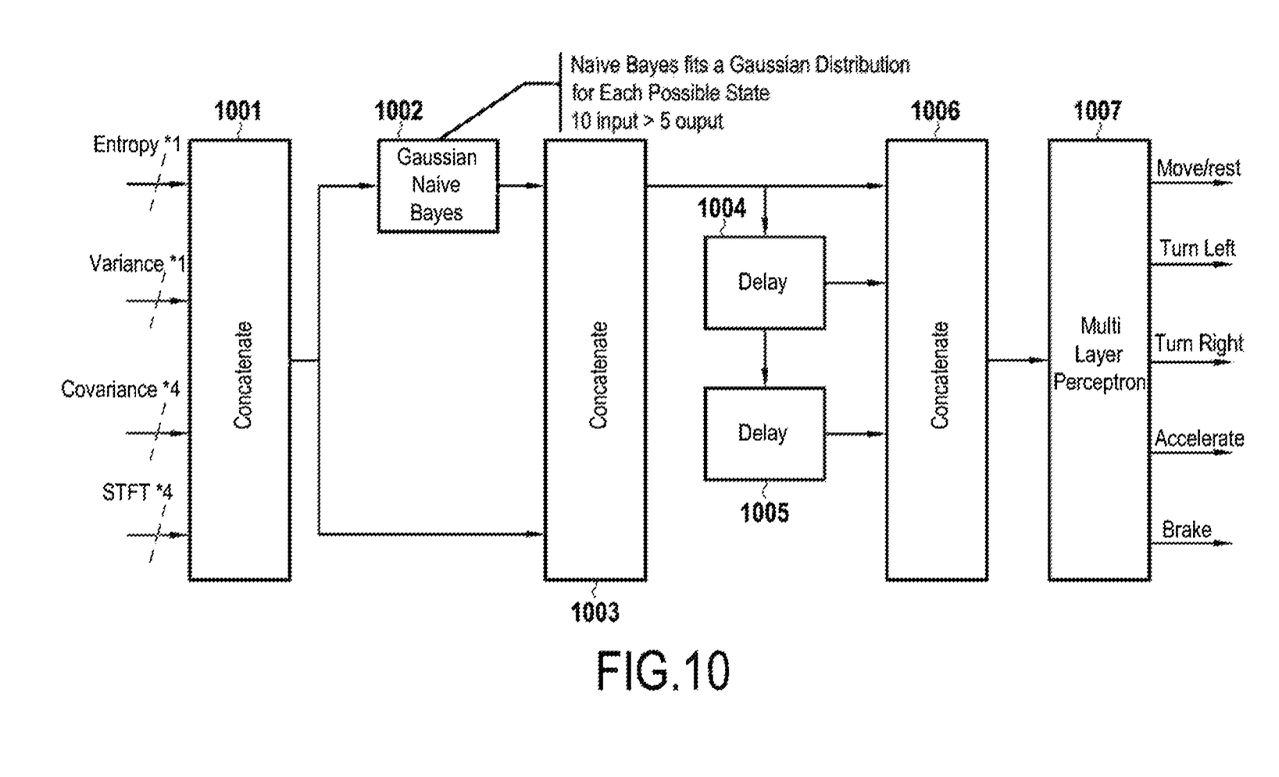
FIG. 10 is a block diagram of a first example of soft classification process.

A first example of soft classification process is shown on FIG. 10. In this example, the preliminary soft predictions obtained using the variances, the differential entropy values, the covariances, and the STFT are used as input. More precisely, there are:
   one input for the differential entropy with a preliminary soft prediction on whether the user intends to move or rest,
   one input for the variances with a preliminary soft prediction on whether the user intends to move or rest,
   a first input for the covariances with a preliminary soft prediction on whether or not the user intends to turn right,
   a second input for the covariances with a preliminary soft prediction on whether or not the user intends to turn left,
   a third input for the covariances with a preliminary soft prediction on whether or not the user intends to accelerate,
   a fourth input for the covariances with a preliminary soft prediction on whether or not the user intends to brake,
   a first input for the STFT with a preliminary soft prediction on whether or not the user intends to turn right,
   a second input for the STFT with a preliminary soft prediction on whether or not the user intends to turn left,
   a third input for the STFT with a preliminary soft prediction on whether or not the user intends to accelerate,
   a fourth input for the STFT with a preliminary soft prediction on whether or not the user intends to brake, These 10 inputs are concatenated in step 1001. Then, in step 1002, a naive Bayes Gaussian layer is used on the preliminary soft predictions to obtain additional preliminary soft predictions each corresponding to a possible driving intention (including rest). The output of the naive Bayes Gaussian layer is concatenated in step 1003 with the output of step 1001.

The output of step 1003 is delayed once in step 1004 (for example with a delay of 0.4 second) and a second time in step 1005 (for example with a delay of 0.4 second).

The outputs of steps 1003, 1004, and 1005 are concatenated in step 1006 and inputted to a multi-layer perceptron 1007.

It should be noted that the concatenation step 1006 is optional.

The multi-layer perceptron delivers five soft predictions (i.e. five values comprised between 0 and 1) on:
   Moving or resting,
   Turning left,
   Turning right,
   Accelerating,
   Braking.

The steps of FIG. 10 allow obtaining a soft classification in a regressive manner, because it uses the concept of memory through an embedding procedure (in which delays are applied).

The steps of FIG. 10 have provided good results on the prediction of the driving intention of the user.

While it is possible not to perform the two delaying steps 1004 and 1005), so as to obtain a non-regressive classifier, the inventors have observed that these two steps improve the quality of the prediction.

The invention claimed is:

1. A method for controlling a vehicle according to electroencephalography (EEG) signals of a user of the vehicle, comprising, on a processor:
    acquiring a plurality of the EEG signals from the user of the vehicle,
    determining values for each feature of a predetermined plurality of features of the EEG signals,
    for each feature of the predetermined plurality of features of the EEG signals, performing a respective preliminary soft classification process by at least one trained predictor, of a plurality of trained predictors, corresponding to the feature and taking the values of the feature as input, so as to obtain a plurality of preliminary soft predictions each predicting one of a plurality of predicted driving intentions, each of the plurality of preliminary soft predictions thereby based on a corresponding one of the predetermined plurality of features of the EEG signals,
    performing a non-preliminary soft classification process by a trained core classifier taking the plurality of preliminary soft predictions as input, so as to obtain a final driving intention of the user, the trained core classifier being previously trained by machine learning,
    wherein the predetermined plurality of features include variances of the EEG signals, differential entropy of the EEG signals, averages of a short-term Fourier transform (STFT) of the EEG signals, and covariances of the EEG signals,
    wherein the plurality of predicted driving intentions include an intention to move or rest, an intention to turn left, an intention to turn right, an intention to accelerate, and an intention to brake, and
    wherein the plurality of trained predictors include:
    a variance-based predictor corresponding to the variances and trained to obtain a preliminary soft prediction of the intention to move or rest, based on the variance values,
    an entropy-based predictor corresponding to the differential entropy and trained to obtain a preliminary soft prediction of the intention to move or rest, based on the differential entropy values,
    a first STFT predictor corresponding to the averages of the STFT and trained to obtain a preliminary soft prediction of the intention to turn left, based on values of the averages of the STFT,
    a second STFT predictor corresponding to the averages of the STFT and trained to obtain a preliminary soft prediction of the intention to turn right, based on the values of the averages of the STFT,
    a third STFT predictor corresponding to the averages of the STFT and trained to obtain a preliminary soft prediction of the intention to accelerate, based on the values of the averages of the STFT,
    a fourth STFT predictor corresponding to the averages of the STFT and trained to obtain a preliminary soft prediction of the intention to brake, based on the values of the averages of the STFT,
    a first covariance predictor corresponding to the covariances and trained to obtain a preliminary soft prediction of the intention to turn left, based on covariance values,
    a second covariance predictor corresponding to the covariances and trained to obtain a preliminary soft prediction of the intention to turn right, based on the covariance values,
    a third covariance predictor corresponding to the covariances and trained to obtain a preliminary soft prediction of the intention to accelerate, based on the covariance values, and
    a fourth covariance predictor corresponding to the covariances and trained to obtain a preliminary soft prediction of the intention to brake, based on the covariance values,
    wherein the method further comprises at least one of:
        controlling the vehicle to turn left based on the final driving intention of the user indicating to turn left,
        controlling the vehicle to turn right based on the final driving intention of the user indicating to turn right,
        controlling the vehicle to accelerate based on the final driving intention of the user indicating to accelerate, and
        controlling the vehicle to brake based on the final driving intention of the user indicating to brake.

2. The method of claim 1, wherein the values for each feature of the predetermined plurality of features of the EEG signals are determined by pre-processing the EEG signals, the pre-processing comprising applying a band-pass filter to the EEG signals, filter passing frequencies of the band-pass filter being within one of the $\alpha$ band, the $\beta$ band, and the $\alpha$ band and the $\beta$ band.

3. The method of claim 2, wherein the pre-processing further comprises applying a common average reference treatment.

4. The method of claim 1, wherein the trained core classifier is a multilayer perceptron.

5. The method of claim 4, further comprising applying at least one delay to the preliminary soft predictions so as to obtain at least one additional input to the non-preliminary soft classification process.

6. The method of claim 1, further comprising using a naive Bayes Gaussian layer on the preliminary soft predictions to obtain additional preliminary soft predictions each corresponding to a possible driving intention, the additional preliminary soft predictions and the preliminary soft predictions being used as input to the non-preliminary soft classification process.

7. The method of claim 6, further comprising applying at least one delay to the preliminary soft predictions and the additional preliminary soft predictions so as to obtain at least one additional input to the non-preliminary soft classification process.

8. A non-transitory recording medium readable by a computer and having recorded thereon a computer program including instructions for executing the method of claim 1.

9. A system for determining a driving intention of a user of a vehicle using electroencephalography (EEG) signals, comprising:
    an acquisition connection interface comprising at least one electrode, the acquisition connection interface configured to acquire a plurality of the EEG signals from the user of the vehicle,
    a processor, and a memory comprising instructions executable by the processor to:

acquire, using the acquisition connection interface, the plurality of the EEG signals from the user of the vehicle, determine values for each feature of a predetermined plurality of features of the EEG signals, for each feature of the predetermined plurality of features of the EEG signals, perform a respective preliminary soft classification process by at least one trained predictor, of a plurality of trained predictors, corresponding to the feature and taking the values of the feature as input, so as to obtain a plurality of preliminary soft predictions each predicting one of a plurality of predicted driving intentions, each of the plurality of preliminary soft predictions thereby based on a corresponding one of the predetermined plurality of features of the EEG signals, perform a non-preliminary soft classification process by a trained core classifier taking the plurality of preliminary soft predictions as input, so as to obtain a final driving intention of the user, the trained core classifier being previously trained by machine learning, wherein the predetermined plurality of features include variances of the EEG signals, differential entropy of the EEG signals, averages of a short-term Fourier transform (STFT) of the EEG signals, and covariances of the EEG signals, wherein the plurality of predicted driving intentions include an intention to move or rest, an intention to turn left, an intention to turn right, an intention to accelerate, and an intention to brake, and wherein the plurality of trained predictors include:

a variance-based predictor corresponding to the variances and trained to obtain a preliminary soft prediction of the intention to move or rest, based on the variance values, an entropy-based predictor corresponding to the differential entropy and trained to obtain a preliminary soft prediction of the intention to move or rest, based on the differential entropy values, a first STFT predictor corresponding to the averages of the STFT and trained to obtain a preliminary soft prediction of the intention to turn left, based on values of the averages of the STFT, a second STFT predictor corresponding to the averages of the STFT and trained to obtain a preliminary soft prediction of the intention to turn right, based on the values of the averages of the STFT, a third STFT predictor corresponding to the averages of the STFT and trained to obtain a preliminary soft prediction of the intention to accelerate, based on the values of the averages of the STFT, a fourth STFT predictor corresponding to the averages of the STFT and trained to obtain a preliminary soft prediction of the intention to brake, based on the values of the averages of the STFT, a first covariance predictor corresponding to the covariances and trained to obtain a preliminary soft prediction of the intention to turn left, based on covariance values, a second covariance predictor corresponding to the covariances and trained to obtain a preliminary soft prediction of the intention to turn right, based on the covariance values, a third covariance predictor corresponding to the covariances and trained to obtain a preliminary soft prediction of the intention to accelerate, based on the covariance values, and a fourth covariance predictor corresponding to the covariances and trained to obtain a preliminary soft prediction of the intention to brake, based on the covariance values, wherein the instructions are further executable by the processor to implement at least one of:

controlling the vehicle to turn left based on the final driving intention of the user indicating to turn left, controlling the vehicle to turn right based on the final driving intention of the user indicating to turn right, controlling the vehicle to accelerate based on the final driving intention of the user indicating to accelerate, and controlling the vehicle to brake based on the final driving intention of the user indicating to brake.

10. A vehicle comprising:

an acquisition connection interface comprising at least one electrode, the acquisition connection interface configured to acquire a plurality of the EEG signals en from a user of the vehicle, a processor, a memory comprising instructions executable by the processor to:

acquire, using the acquisition connection interface, the plurality of the EEG signals from the user of the vehicle, determine values for each feature of a predetermined plurality of features of the EEG signals, for each feature of the predetermined plurality of features of the EEG signals, perform a respective preliminary soft classification process by at least one trained predictor, of a plurality of trained predictors, corresponding to the feature and taking the values of the feature as input, so as to obtain a plurality of preliminary soft predictions each predicting one of a plurality of predicted driving intentions, each of the plurality of preliminary soft predictions thereby based on a corresponding one of the predetermined plurality of features of the EEG signals, perform a non-preliminary soft classification process by a trained core classifier taking the plurality of preliminary soft predictions as input, so as to obtain a final driving intention of the user, the trained core classifier being previously trained by machine learning, wherein the predetermined plurality of features include variances of the EEG signals, differential entropy of the EEG signals, averages of a short-term Fourier transform (STFT) of the EEG signals, and covariances of the EEG signals, wherein the plurality of predicted driving intentions include an intention to move or rest, an intention to turn left, an intention to turn right, an intention to accelerate, and an intention to brake, and wherein the plurality of trained predictors include:

a variance-based predictor corresponding to the variances and trained to obtain a preliminary soft prediction of the intention to move or rest, based on the variance values, an entropy-based predictor corresponding to the differential entropy and trained to obtain a preliminary soft prediction of the intention to move or rest, based on the differential entropy values, a first STFT predictor corresponding to the averages of the STFT and trained to obtain a preliminary soft prediction of the intention to turn left, based on values of the averages of the STFT, a second STFT predictor corresponding to the averages of the STFT and trained to obtain a preliminary soft prediction of the intention to turn right, based on the values of the averages of the STFT, a third STFT predictor corresponding to the averages of the STFT and trained to obtain a preliminary soft prediction of the intention to accelerate, based on the values of the averages of the STFT, a fourth STFT predictor corresponding to the averages of the STFT and trained to obtain a preliminary soft prediction of the intention to brake, based on the values of the averages of the STFT, a first covariance predictor corresponding to the covariances and trained to obtain a preliminary soft prediction of the intention to turn left, based on covariance values, a second covariance predictor corresponding to the covariances and trained to obtain a preliminary soft prediction of the intention to turn right, based on the covariance values, a third covariance predictor corresponding to the covariances and trained to obtain a preliminary soft prediction of the intention to accelerate, based on the covariance values, and a fourth covariance predictor corresponding to the covariances and trained to obtain a preliminary soft prediction of the intention to brake, based on the covariance values, wherein the instructions are further executable by the processor to implement at least one of:

controlling the vehicle to turn left based on the final driving intention of the user indicating to turn left, controlling the vehicle to turn right based on the final driving intention of the user indicating to turn right, controlling the vehicle to accelerate based on the final driving intention of the user indicating to accelerate, and controlling the vehicle to brake based on the final driving intention of the user indicating to brake.

* * * * *